United States Patent [19]
Lee et al.

[11] Patent Number: 6,120,754
[45] Date of Patent: *Sep. 19, 2000

[54] REMINERALIZATION OF TEETH

[75] Inventors: G. Jae Lee, Trumbull; Alexander George Ziemkiewicz, Shelton; David Robert Williams, Monroe; Stephen Roy Barrow, Trumbull, all of Conn.

[73] Assignee: Chesebrough-Pond's USA Co., division of Conopco, Inc., Greenwich, Conn.

[*] Notice: This patent is subject to a terminal disclaimer.

[21] Appl. No.: 09/217,094

[22] Filed: Dec. 21, 1998

Related U.S. Application Data

[60] Provisional application No. 60/077,627, Mar. 11, 1998.

[51] Int. Cl.$^7$ .............................. A61K 7/16; A61K 7/18
[52] U.S. Cl. .................. 424/49; 424/52; 424/57
[58] Field of Search .................. 424/49, 52, 57

[56] References Cited

U.S. PATENT DOCUMENTS

| | | |
|---|---|---|
| 4,080,440 | 3/1978 | DiGiulio et al. . |
| 4,183,915 | 1/1980 | Gaffar et al. . |
| 4,460,565 | 7/1984 | Weststrate et al. . |
| 4,885,155 | 12/1989 | Parran, Jr. et al. . |
| 5,020,694 | 6/1991 | Pettengill . |
| 5,037,639 | 8/1991 | Tung . |
| 5,041,280 | 8/1991 | Smigel . |
| 5,059,417 | 10/1991 | Williams et al. . |
| 5,085,853 | 2/1992 | Williams et al. . |
| 5,171,564 | 12/1992 | Nathoo et al. . |
| 5,268,167 | 12/1993 | Tung . |
| 5,372,802 | 12/1994 | Barrows et al. . |
| 5,372,803 | 12/1994 | Williams et al. . |
| 5,437,857 | 8/1995 | Tung . |
| 5,531,983 | 7/1996 | Van Velthuijsen . |
| 5,534,244 | 7/1996 | Tung . |
| 5,571,502 | 11/1996 | Winston et al. . |
| 5,599,527 | 2/1997 | Hsu et al. . |
| 5,603,922 | 2/1997 | Winston et al. . |
| 5,605,675 | 2/1997 | Usen et al. . |
| 5,614,175 | 3/1997 | Winston et al. . |
| 5,698,182 | 12/1997 | Prencipe et al. . |
| 5,833,957 | 11/1998 | Winston et al. . |
| 5,858,333 | 1/1999 | Winston et al. . |
| 5,866,102 | 2/1999 | Winston et al. . |
| 5,891,448 | 4/1999 | Chow et al. . |
| 5,895,641 | 4/1999 | Usen et al. . |

FOREIGN PATENT DOCUMENTS

| | | |
|---|---|---|
| 0 520 545 | 6/1992 | European Pat. Off. . |
| 0 559 262 | 2/1993 | European Pat. Off. . |
| 2 164 383 | 12/1971 | Germany . |
| 9143043 | 6/1997 | Japan . |
| 1090340 | 3/1965 | United Kingdom . |
| 1 408 922 | 10/1975 | United Kingdom . |
| 96/20693 | 7/1996 | WIPO . |
| 97/06774 | 2/1997 | WIPO . |

OTHER PUBLICATIONS

Http://www.Enamelon.com/Prof/PF/SS.Htm Latest Clinical Data "Enamelon"® (Jul. 8, 1999).
Abstracts From Enamelon Website.
Hall et al. Caries Res 32:312, 1998.
Kleber et al. J. Dent. Res 77 (Spec Iss B) 843, 1998.
Tanzer et al. Caries Res 31:288, 1997.
Mundorf et al J. Dent. Res. 77 (Spec.Iss. A):246, 1998.
Schemehorn et al J. Dent. Res 77 (Spec. Iss A): 188, 1998.
Schemehorn et al J. Dent.Res 76 (Spec. Iss):376, 1997.
Tanzer et al J. Dent. Res. 76 (Spec. Iss:):134, 1997.
Munoz et al J. Dent. Res. 77 (Spec. Iss. A):242, 1998.
Yaskell et al J. Dent. Res. 77 (Spec. Iss. A): 188, 1998.
Wolinsky et al J. Dent. Res.77(Spec. Iss. A):246, 1998.
Kardos et al. J. Dent. Res. 77 (Spec. Iss.A):246, 1998.
Snagne–Agnero et al J. Dent Res. 76 (Spec. Iss):255, 1997.
Rosenblum et al J. Dent. Res 76(Spec. Iss.):17, 1997.
Soap/Cosmetics/Chemical Specialties "Beyond Fluoride, The Enamelon Phenomenon"—p. 66, Jun. 1998.

*Primary Examiner*—Shep K. Rose
*Attorney, Agent, or Firm*—Milton L. Honig

[57] ABSTRACT

An oral product and method is provided for remineralizing teeth. The product includes a first composition containing a water soluble calcium phosphate salt or monolithic combination of calcium and phosphate salts in a carrier with the first composition having a pH less than 7, and a second composition containing an alkaline material and a fluoride ion source in a carrier to achieve a pH greater than 7.5. The first and second compositions are separated from one another prior to use. When combined upon application to teeth, the first and second compositions generate hydroxyapatite depositing same on dental enamel.

18 Claims, No Drawings

REMINERALIZATION OF TEETH

This Appln claims the benefit of U.S. Provisional No. 60/077,627 filed Mar. 11, 1998.

BACKGROUND OF THE INVENTION

1. Field of the Invention

The invention relates to oral compositions and methods employing such compositions for the remineralization of dental enamel.

2. The Related Art

In the mouth, there is a natural equilibrium between hydroxyapafite being dissolved from the enamel of teeth and hydroxyapatite being formed on or in the teeth from substances occurring naturally in the saliva. This equilibrium is shifting continuously. Among other factors, it is determined by diet and physical condition. If the equilibrium is such that hydroxyapatite is dissolved, a cariogenic condition arises which is referred to as demineralization. If the equilibrium is such that hydroxyapatite is being formed in demineralized enamel, this is referred to as remineralization. By remineralization, pre-existing tooth decay and caries can be reduced or eliminated by natural means.

It has long been known that fluoride-providing compounds, even in low concentrations, promote the remineralization process. They thereby reduce pre-existing carious conditions in the tooth structure. Fluoride is most effective during the developmental years from childhood to young adulthood. Improved remedies are necessary, especially beyond the formative years.

Attempts have been made to arrest or prevent progression of caries by incorporation of calcium and phosphate ions through dietary and dentifrice means. A significant hurdle to this approach has been maintaining the calcium and phosphate ions available in a non-precipitated form. Two phase or separately compartmented calcium and phosphate compositions have been proposed. GB Patent 1,408,922 (Raff et al.) suggests a two-compartment tube, the first being filled with a toothpaste containing calcium chloride and the second containing disodium hydrogen phosphate. Upon dispensing, the compositions are mixed thereby causing the precipitation of calcium phosphate onto the teeth.

A similar approach is reported by Tung in U.S. Pat. No. 5,037,639 and U.S. Pat. No. 5,268,167. The restorative compositions disclosed therein employ amorphous calcium phosphate or solutions which will form amorphous calcium phosphate suspended in a carrier. Suitable carriers were said to include gels, chewing gum, powders, mouthrinses, carbonated solutions and toothpaste. These compositions are said to have long range structure; however, they are thought to be homogeneous when measured on an Angstrom Scale. Under physiological conditions the amorphous calcium compounds have high solubilities, high formation rates and high rates of conversion to apatite. The rates of formation and conversion allow remineralization of the dental tissue to occur at a greater speed. Doubts have been raised however with respect to the efficacy of such treatment. Better systems need to be developed.

Accordingly, it is an object of the present invention to provide an oral product and method for building stronger, healthier teeth.

Another object of the present invention is to provide an oral product and method for remineralizing enamel which can be accomplished by a consumer without intervention of a dentist.

These and other objects of the present invention will become more readily apparent through the following summary and detailed discussion.

SUMMARY OF THE INVENTION

An oral product is provided for remineralizing teeth which includes:

(i) a first composition comprising from about 0.01 to about 30% by weight of a water-soluble calcium phosphate or monolithic combination of water soluble calcium and phosphate salts, the composition having a pH less than 7; and (ii) a second composition including from about 0.01 to about 30% by weight of an alkaline material and an anticaries effective amount of a fluoride ion source, the second composition having a pH greater than 7.5 and stored separately from the first composition in a manner to avoid contact between the phosphate and the alkaline material.

DETAILED DESCRIPTION OF THE INVENTION

Unlike much of the previous technology, it has been found that remineralization products do not need to separate calcium from phosphate ions in a storage system prior to use. Now it has been discovered that a water soluble calcium phosphate salt can be stored within one composition held at a low pH. Activation of this composition to deposit hydroxyapatite onto teeth is achieved by mixing this first composition with a second composition containing fluoride and having a high pH.

Although not wishing to be bound by any theory, it is theorized that upon mixing against the teeth, the soluble calcium phosphate of the first composition interacts with fluoride of the second composition. The alkaline environment of the second composition then causes precipitation of a calcium fluoro phosphate amorphous salt. Transformation of a monocalcium salt cascades downward to the di, octa and then eventually fluoridated hydroxyapatite in the presence of the high pH. Preferably fluoride should only be in the second composition so that it co-precipitates as an element of hydroxyapatite.

Separate storage of the two compositions of this invention may be accomplished through a dual compartment dispenser. U.S. Pat. No. 4,687,663 (Schaeffer) discloses a dual-compartment package respectively storing a peroxide gel and a bicarbonate paste. Pump packaging with multiple compartments is reported in U.S. Pat. No. 5,038,963 (Pettengill et al.) and U.S. Pat. No. 5,020,694 (Pettengill) which are embodied in a U.S. product known as Mentadent® Baking Soda & Peroxide.

Of course, delivery of compositions according to the present invention is not limited to unitary albeit multicompartmented dispensers nor to totally segregated compartments. The dispenser may be a system in the form of two individual tubes quite separate from one another but packaged within a kit. Ribbons of the dentifrice from each tube are delivered to a toothbrush with mixing of the compositions occurring in the mouth. Delivery may also be from a single chambered tube except that each of the two compositions are semi solid strips positioned side-by-side touching but not mixing with one another. The relatively high viscosity of the products prevents any substantial transference of either pH change or components between the two strips. Illustrative of this technology is a U.S. product sold by Colgate® under the Baking Soda & Peroxide brand. Still another method of delivery may be a single composition such as a paste or gel housing an alkaline environment. Monocalcium phosphate compositions may be dispersed throughout the alkaline composition yet separated from contact by a coating encapsulating the phosphate. Activation occurs in the mouth through the presence of water or saliva which penetrates the encapsulating coating releasing phosphate salt to interact with the alkaline environment.

A critical component of the first composition of this invention is a water soluble calcium phosphate salt. By the term "water soluble" is meant a solubility of at least 0.1 gram in 100 ml water at 25° C. Most preferred is monocalcium hydrogen phosphate but also of potential use are calcium polyol phosphates (e.g. calcium glycerophosphate) and monocalcium ammonium phosphate salts. Monolithic compositions of water soluble calcium and phosphate salts may be employed as alternatives to pre-formed water soluble calcium phosphates. By the term "monolithic" is meant separate water soluble calcium salts and phosphate salts which from solution may metathesize into calcium phosphates in solution or later upon mixing with the second composition. Illustrative calcium salts include the halides, sulphates, nitrates, citrates, sugars and $C_1$–$C_6$ carboxylates. Most preferred is calcium chloride, calcium sulphate and calcium acetate. The monolithic partner phosphate salts may be alkali, ammonium or combination salts thereof. Examples include sodium ammonium phosphate, sodium phosphate, ammonium phosphate and potassium phosphate. The water-soluble calcium phosphate salts or the monolithic calcium and phosphate salts (by weight of calcium and phosphate ions only) may be present in amounts ranging from 0.01 to 30%, preferably from 0.1 to 20%, optimally from 1 to 10% by weight of the first composition.

Solubility of the phosphate salt is maintained in the first composition by having an acidic environment. The pH will be less than 7, preferably from 1 to 6.5, more preferably from 1.8 to 6, optimally from 2.5 to 5.5.

The second composition of the present invention requires an alkaline material so that the second composition has a pH greater than 7, preferably from 7.2 to 11, more preferably from 8 to 10, optimally from 8.5 to 9.5. Alkaline materials suitable to achieve the pH are sodium bicarbonate, potassium bicarbonate, sodium carbonate, potassium carbonate, calcium carbonate, calcium oxide, sodium hydroxide, potassium hydroxide and mixtures thereof. Amounts of the alkaline material may range from 0.1 to 60%, preferably from 0.5 to 30%, more preferably from 1 to 20%, optimally from 3 to 15% by weight of the second composition.

An important further component of the second composition is a fluoride anticaries compound. Illustrative of such fluoride compounds are sodium fluoride, potassium fluoride, calcium fluoride, magnesium fluoride, stannous fluoride, stannous monofluorophosphate, sodium monofluorophosphate and copper fluoride. Most preferred is sodium fluoride. These sources should release anywhere from about 25 to about 5,000 ppm of fluoride ion. The anticaries compound will normally be present in an amount from about 0.01 to about 5%, preferably from 0.1 to 2.5%, optimally from 0.2 to 1.5% by weight of combined first and second compositions.

The compositions of the present invention may be in the form of either a toothpaste, gel, powder or mouthwash. Most preferably the compositions are either pastes or gels. Especially suitable is where the phosphate salt is incorporated in a gel and the alkaline material incorporated into a paste. These compositions may include water or be anhydrous.

The phosphate salt as well as the alkaline material will be delivered through a pharmaceutically acceptable carrier. The term "pharmaceutically acceptable carrier" will include such functional ingredients as water, humectants, abrasives, thickeners, surfactants and combinations thereof. Total levels of these materials may range anywhere from about 1 to about 99%, preferably from 20 to 80%, optimally from 30 to 60% by weight.

Acidity in the first composition may be achieved by formulating with a peroxide such as hydrogen peroxide, inorganic acids such as phosphoric, hydrochloric, nitric or boric acids, and organic $C_2$–$C_{20}$ carboxylic acids such as citric, malic, lactic, alginic, succinic, tartaric and ascorbic acids. Soluble salts may also be employed such as potassium bitartrate, sodium acid citrate, acid phosphate and pyrophosphate salts such as monosodium phosphate and disodium pyrophosphate. Levels of the acidity inducing substances may range in amounts from about 0.1 to about 20%, preferably from about 0.5 to about 10%, optimally from 1.0 to 8% by weight of the first composition. Hydrogen peroxide and phosphoric acid are the preferred substances.

Among the carriers, water when present may range in amounts from about 1 to 95%, preferably from 20 to 60%, optimally from 30 to 50% by weight of each of the compositions. Of course some formulations may be anhydrous.

Humectants are usually also present as one of the carriers. Illustrative of this category are sorbitol, maltitol, mannitol, glycerin and polyethylene glycols (e.g. Carbowax). Amounts of the humectant may range from 1 to 60%, preferably from about 5 to about 50%, optimally from 10 to 40% by weight of each composition.

Abrasives are normally present in toothpastes and some gels. These may include sodium metaphosphate, dicalcium phosphate (which is not considered a water-soluble phosphate), calcium pyrophosphate, silica, alumina, chalk, insoluble bicarbonate salts, and mixtures thereof. Amounts of the abrasives may range from about 1 to about 80%, preferably from 5 to 50% by weight of each composition.

Thickeners are a further type of carrier which can be included in the compositions of this invention. Illustrative thickeners such as sodium carboxy-methyl cellulose, hydroxy ethyl cellulose, methyl cellulose, ethyl cellulose, gum tragacanth, gum arabic, gum karaya, sodium alginate, carrageenan, guar, xanthan gum, Irish moss, starch, modified starch, Carbomers (crosslinked acrylates) and mixtures thereof. Inorganic substances may also be suitable, especially silica aerogels and magnesium aluminum silicate (e.g. Veegum). Amounts of the thickener may range from about 0.01 to about 30%, preferably from 0.1 to 20%, optimally from 0.5 to 15% by weight of a composition.

Surfactants are also considered to be within the carrier definition. Surfactants may either be anionic, nonionic, cationic or amphoteric. Most preferred are sodium lauryl sulphate, sodium dodecylbenzene sulphonate and sodium lauryl sarcosinate. Surfactants may be present in an amount from about 0.5 to about 10%, preferably from 0.8 to 5% by weight of a composition.

Gel compositions are structured with substances than can be characterized as either humectants or surfactants. For instance, a typical gel structurant is a polyoxyethylene-polyoxypropylene copolymer such as those sold by the BASF Corporation under the trademark Pluronic® F88, F99, F108 and F127. These materials are also known as Poloxamers and employed in amounts from about 5 to about 30%, preferably between about 18 and about 25% by weight of a composition.

Flavors may also be present in the compositions. These flavors may be based on oils of spearmint and peppermint. Examples of other flavoring materials include menthol, clove, wintergreen, eucalyptus and aniseed. Flavors may range in concentration from about 0.1 to about 5% by weight of a composition.

Sweetening agents may also be included such as saccharin, sodium cyclamate, aspartame, ace-sulfame, xylitol and combinations thereof at levels from 0.1 to 10% by weight of a composition.

Gel compositions incorporating hydrogen peroxide may include a sequestering agent(s) such as a pyrophosphate or other phosphate for chelation of ferric/ferrous ion as well as other transition metal ions to enhance hydrogen peroxide stability. The sequestering agents may also be included within the paste compositions and are present in amounts from about 0.01 to about 20% by weight of a composition. Most preferred chelatants are tetrasodium pyrophosphate, sodium tripolyphosphate and sodium hexametaphosphate, all known to be effective at lower pH with little affinity for calcium ion. Other organic chelating agents such as sodium citrate and zinc citrate are also useful.

Other additives may also be incorporated such as preservatives, silicones, other synthetic or natural polymers such as Gantrez S97®, antitartar actives and antigingivitis actives. Among the antitartar agents are included zinc citrate, tetrasodium pyrophosphate, disodium pyrophosphate, dipotassium pyrophosphate, tetrapotassium pyrophosphate and mixtures thereof. Antigingivitis actives may include thymol, Triclosan, stannous gluconate and mixtures thereof. Amounts of each of the aforementioned ingredients will depend upon their function. Generally each of these substances will range in amounts from about 0.01 to about 20% by weight of a composition.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight of either the first or second composition unless otherwise indicated.

EXAMPLE 1

Typical of the present invention is a first composition in the form of a gel and a second composition in the form of a paste. Each of these formulations is held in a separate compartment of a dual-compartment dispenser similar to that disclosed in U.S. Pat. No. 5,038,963 (Pettengill et al.).

| Gel Composition 1A | |
|---|---|
| INGREDIENT | WEIGHT % |
| Glycerin | 40.00 |
| Pluronic F-127 | 20.00 |
| Monocalcium Phosphate Monohydrate | 5.00 |
| Hydrogen Peroxide (35% Active) | 4.285 |
| Phosphoric Acid | 0.650 |
| Tetrasodium Pyrophosphate | 0.50 |
| FD&C Blue No. 1 | 0.01 |
| Water | Balance |

| Paste Composition 1B | |
|---|---|
| INGREDIENT | WEIGHT % |
| Polyol II (70% Sorbitol) | 40.50 |
| Syloid 63XX (Hydrated Silica) | 15.00 |
| Sodium Bicarbonate | 10.00 |
| Sylox 15X | 6.00 |
| Polyethylene Glycol 1450 (PEG-32) | 3.00 |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |
| Titanium Dioxide | 0.30 |
| Water | Balance |

EXAMPLE 2

Another system typical of the present invention is a two part toothpaste. Each part is placed in a dual-compartment dispenser similar to that of Example 1.

| COMPONENTS | PASTE 2A (% WEIGHT) | PASTE 2B (% WEIGHT) |
|---|---|---|
| Sorbitol (70% Active) | 28.50 | — |
| Syloid 63XX (Hydrated Silica) | 20.00 | 18.0 |
| Glycerin | 28.00 | 32.0 |
| Monocalcium Phosphate | 6.49 | — |
| Citric Acid | 5.00 | — |
| Syloid 244 (Thickening Silica) | 3.00 | 0.5 |
| Xanthan Gum | 0.50 | — |
| Sodium Fluoride | — | 0.44 |
| FD&C Blue No. 1 | 0.01 | — |
| Sodium Bicarbonate | — | 25.0 |
| Sodium Lauryl Sulphate | — | 1.5 |
| Sodium Carboxymethyl Cellulose | — | 0.8 |
| Flavor | — | 1.0 |
| Titanium Dioxide | — | 0.4 |
| Sodium Saccharin | — | 0.2 |
| Water | balance | balance |

The pH of Paste 2A is approximately 2.0. Paste 2B has a pH of approximately 9.0. Strips of each of these are extruded onto a toothbrush. These strips are then brushed against the teeth thereby mixing them together. Hydroxyapatite is formed in the mixing process and deposits onto the teeth.

EXAMPLE 3

Yet another system typical of the present invention is a two part toothpaste as described below. Each part is placed in a dual-compartment dispenser similar to that of Example 1.

| COMPONENTS | PASTE 3A (% WEIGHT) | PASTE 3B (% WEIGHT) |
|---|---|---|
| Sorbitol (70% Active) | 30.50 | — |
| Alumina | 20.00 | 18.0 |
| Polyol II | 10.00 | 32.0 |
| Malic Acid | 5.00 | — |
| Monocalcium Phosphate | 4.50 | — |
| Syloid 244 (Thickening Silica) | 3.00 | 0.5 |
| Xanthan Gum | 0.50 | — |

-continued

| COMPONENTS | PASTE 3A (% WEIGHT) | PASTE 3B (% WEIGHT) |
|---|---|---|
| Sodium Fluoride | — | 0.44 |
| FD&C Blue No. 1 | 0.01 | — |
| Sodium Bicarbonate | — | 25.0 |
| Sodium Lauryl Sulphate | — | 1.5 |
| Sodium Carboxymethyl Cellulose | — | 0.8 |
| Flavor | — | 1.0 |
| Sodium Carbonate | — | 0.4 |
| Sodium Saccharin | — | 0.2 |
| Water | balance | balance |

The pH of Paste 3A and 3B respectively are approximately 2 and 9. Strips of each of these pastes are placed onto a toothbrush. These strips are then brushed against the teeth thereby mixing them together. Hydroxyapatite is formed in the mixing process and deposits on the teeth.

EXAMPLE 4

This Example illustrates use of a monolithic calcium and phosphate salt combination to deliver the water soluble monocalcium phosphate component. Separate gel and paste formulations representing the first and second compositions of this invention were prepared with the following compositions.

Gel Composition 4A

| INGREDIENT | WEIGHT % |
|---|---|
| Glycerin | 40.00 |
| Pluronic F-127 ® | 20.00 |
| Hydrogen Peroxide (35% Active) | 4.29 |
| Calcium Chloride Dihydrate | 2.10 |
| Dibasic Sodium Phosphate | 1.00 |
| Phosphoric Acid (85% Active) | .50 |
| Sodium Citrate | 0.53 |
| FD&C Blue No. 1 | 0.01 |
| Water | Balance |

Paste Composition 4B

| INGREDIENT | WEIGHT % |
|---|---|
| Polyol II (70% Sorbitol) | 40.50 |
| Syloid 63XX (Hydrated Silica) | 15.00 |
| Sodium Bicarbonate | 10.00 |
| Sylox 15X | 6.00 |
| Polyethylene Glycol 1450 (PEG-32) | 3.00 |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |
| Titanium Dioxide | 0.30 |
| Water | Balance |

EXAMPLE 5

Yet another system typical of the present invention is a two part toothpaste as described below. Each part is placed in a dual compartment dispenser similar to that of Example 1.

Gel Composition 5A

| INGREDIENT | WEIGHT % |
|---|---|
| Glycerin | 40.00 |
| Pluronic F-127 | 20.00 |
| Monocalcium Phosphate Monohydrate | 3.10 |
| Phosphoric Acid (85% Active) | 0.85 |
| Water | Balance |

Past Composition 5B

| INGREDIENT | WEIGHT % |
|---|---|
| Polyol II (70% Sorbitol) | 46.68 |
| Syloid 63XX (Hydrated Silica) | 15.00 |
| Sodium Carbonate | 6.50 |
| Sylox 15X (Hydrated Silica) | 6.00 |
| Polyethylene Glycol 1450 (PEG 32) | 5.00 |
| Ethyl Alcohol 38B | 2.84 |
| Sodium Lauryl Sulphate | 2.98 |
| Flavor | 1.00 |
| Cellulose Gum | 0.80 |
| Sodium Saccharin | 0.50 |
| Menthol | 0.50 |
| Sodium fluoride | 0.44 |
| Titanium Dioxide | 0.30 |
| Water | Balance |

The pH of 5A and 5B respectively are approximately 2.7 and 9.5

EXAMPLE 6

This Example illustrates use of monocalcium phosphate in a Gel composition along with Triclosan solubilized in alcohol.

Gel Composition 6A

| INGREDIENT | WEIGHT % |
|---|---|
| Glycerin | 40.00 |
| Pluronic F-127 | 20.00 |
| Alcohol SDA 38B | 5.00 |
| Monocalcium Phosphate, Monohydrate | 1.55 |
| Phosphoric Acid (95% Active) | 0.45 |
| Hydrogen Peroxide (35% Active) | 4.29 |
| Irgacare ® MP (Triclosan) | 0.67 |
| Water | Balance |

Past Composition 6B

| INGREDIENT | WEIGHT % |
|---|---|
| Polyol II (70% Sorbitol) | 46.68 |
| Syloid 63XX (Hydrated Silica) | 15.00 |
| Sodium Bicarbonate | 10.00 |
| Sylox 15X (Hydrated Silica) | 6.00 |
| Polyethylene Glycol 1450 (PEG 32) | 3.00 |
| Ethyl Alcohol 38B | 2.84 |
| Sodium Lauryl Sulphate | 2.98 |
| Flavor | 1.10 |
| Cellulose Gum | 0.80 |
| Sodium Saccharin | 0.54 |
| Menthol | 0.50 |
| Sodium Fluoride | 0.44 |

-continued

| Past Composition 6B | |
|---|---|
| INGREDIENT | WEIGHT % |
| Titanium Dioxide | 0.30 |
| Water | Balance |

The pH of 6A and 6B respectively are approximately 2.7 and 9.2

EXAMPLE 7

Another Example is shown using monocalcium phosphate in a Gel composition. Here Triclosan is incorporated into a Paste composition of elevated pH for eventual combination with the Gel.

| Gel Composition 7A | |
|---|---|
| INGREDIENT | WEIGHT % |
| Glycerin | 40.00 |
| Pluronic F-127 | 20.00 |
| Hydrogen Peroxide (35% Active) | 4.29 |
| Monocalcium Phosphate, Monohydrate | 3.10 |
| Phosphoric Acid (95% Active) | 0.85 |
| Water | Balance |

| Paste Composition 7B | |
|---|---|
| INGREDIENT | WEIGHT % |
| Polyol II | 38.50 |
| Syloid 63XX (Hydrated Silica) | 30.00 |
| IPA* | 15.00 |
| Sodium Carbonate | 7.00 |
| Sylox 15X (hydrated Silica) | 2.00 |
| Ethyl Alcohol 38B | 2.84 |
| Sodium Lauryl Sulphate | 2.98 |
| Flavor | 1.30 |
| Irgacare ® MP (Triclosan) | 0.55 |
| Sodium Saccharin | 0.54 |
| Cellulose Gum | 0.80 |
| Menthol | 0.50 |
| Sodium fluoride | 0.44 |
| Titanium Dioxide | 0.30 |
| Water | Balance |

The pH of 6A and 6B respectively are approximately 2.7 and 9.2

EXAMPLE 8

Calcium phosphate remineralization technology according to the present invention was evaluated both through in vivo and in vitro tests. Results are presented below.

A) Animal Caries

Summary of Experimental Design: Sprague Dawley rats were infected with caries producing bacteria, then treated with slurries of experimental products for three weeks. The animals were also fed a cariogenic diet high in sugar. At end of treatment phase, teeth were scored for caries with total enamel caries incidence being the primary anticaries efficacy variable.

| TOTAL ENAMEL CARIES INDICENCE-1100 ppm F as NaF | | |
|---|---|---|
| TEST CELL | N | MEAN ± SEM |
| Non-Fluoride BS + P Dentifrice* | 40 | 35.83 ± 1.33 |
| NaF BS + P Dentifrice** | 40 | 28.63 ± 1.70 |
| NaF BS + P Dentifrice + Ca and PO$_4$*** | 40 | 24.23 ± 1.27 |

*Dual phase silica base Baking Soda + Peroxide toothpaste without Fluoride.
**Dual phase silica base Baking soda + Peroxide toothpaste with 1,000 ppm Fluoride ion from NaF.
***NaF dual phase silica base Baking Soda + Peroxide toothpaste with 1,200 ppm Ca, 8,000 ppm PO$_4$ and 1,100 ppm F ions.

From the Table it is seen that the sodium fluoride formulation was significantly better for caries protection than the non-fluoride placebo. Yet even more efficient was sodium fluoride in combination with calcium and phosphate in a system according to the present invention and as embodied in Example 1.

B) In Vitro Remineralization Studies

Summary of Experimental Design: Human enamel specimens were prepared to have artificial caries-like lesions. The specimens had their initial surface hardness measured before initiation of the treatment phase. The cyclic treatment regimen consisted of treatment, remineralization and demineralization phases over the course of 21 days. At the end of the treatment regimen, the specimen surface hardness was remeasured. The change in their Vickers Hardness Numbers (Delta VHN) indicated the degree of remineralization provided by the test products.

| In Vitro Remineralization (1100 ppm F as NaF) | | |
|---|---|---|
| TEST CELL | N | DELTA VHN MEAN ± SEM |
| Non-Fluoride BS + P Dentifrice* | 18 | −6 ± 2 |
| NaF Dentifrice** | 18 | 22 ± 2 |
| NaF BS + P Dentifrice + Ca and PO$_4$*** | 18 | 30 ± 3 |
| NaF BS + P Dentifrice + Ca, PO$_4$ and Zinc Citrate**** | 18 | 35 ± 4 |

* Dual phase silica base Baking Soda + Peroxide toothpaste without Fluoride.
** Sodium Fluoride silica base toothpaste (USP Ref. Standard with 1,100 ppm Fluoride)
*** NaF dual phase silica base Baking Soda + Peroxide toothpaste with 1,200 ppm Ca, 8,000 ppm PO$_4$, 1,100 ppm Fluoride ion.
**** NaF dual phase silica base Baking Soda + Peroxide toothpaste with 1,200 ppm Ca, 8,000 pm PO$_4$, 1,100 ppm Fluoride ion and 6,000 ppm Zn (as 2% zinc citrate)

As in the in vivo studies, sodium fluoride as expected was better than the placebo having no fluoride. Incorporation of calcium and phosphate in accordance with the present invention and as shown in the system under Example 1 significantly improved teeth hardness relative to the same system containing only sodium fluoride. An even greater improvement in hardness was evidenced by the further addition of zinc citrate.

In Vitro Remineralization (1500 ppm F as Sodium Monofluorophosphate)

| TEST CELL | N | DELTA VHN MEAN ± SEM |
|---|---|---|
| Non-Fluoride BS + P Dentifrice* | 18 | 32 ± 2 |
| MFP Dentifrice** | 18 | 41 ± 3 |
| MFP BS + P Dentifrice + Ca and PO$_4$*** | 18 | 49 ± 3 |

* Dual phase silica base Baking Soda + Peroxide toothpaste without Fluoride
** MFP silica base toothpaste (USP Ref. Standard with 1,500 ppm Fluoride)
****MFP dual phase silica base Baking Soda + Peroxide toothpaste with 2,500 ppm Ca, 16,000 ppm PO$_4$ and 1,500 ppm Fluoride ion.

Sodium monofluorophosphate as expected was better for improving tooth hardness than a placebo without fluoride. Addition of calcium and phosphate according to the present invention significantly enhanced the activity of sodium monofluorophosphate.

The foregoing description and examples illustrate selected embodiments of the present invention. In light thereof variations and modifications will be suggested to one skilled in the art, all of which are within the spirit and purview of this invention.

What is claimed is:

1. An oral product for remineralizing teeth comprising:
   (i) a first composition comprising from about 0.1 to about 20% by weight of a peroxide compound and from about 0.01 to about 30% by weight of a water-soluble calcium phosphate or monolithic combination of water soluble calcium and phosphate salts, the composition having a pH less than 7; and
   (ii) a second composition including from about 0.01 to about 30% by weight of an alkaline material and an anticaries effective amount of a fluoride ion source, the second composition having a pH greater than 7.5 and stored separately from the first composition in a manner to avoid contact between the phosphate and the alkaline material.

2. The product according to claim 1 wherein the water-soluble phosphate salt is monocalcium hydrogen phosphate.

3. The product according to claim 1 wherein the alkaline material is selected from the group consisting of sodium bicarbonate, potassium bicarbonate, sodium hydroxide, potassium hydroxide, sodium carbonate, potassium carbonate, calcium carbonate, calcium oxide and mixtures thereof.

4. The product according to claim 1 wherein the pH of the first composition ranges from 2.5 to 5.5.

5. The product according to claim 1 wherein the pH of the second composition ranges from 7.2 to 11.

6. The product according to claim 1 wherein the pH of the first composition results from inclusion of a compound selected from the group consisting of hydrogen peroxide, inorganic acids, $C_2$–$C_{20}$ carboxylic acids and mixtures thereof.

7. The product according to claim 1 wherein the monolithic combination of water soluble calcium salts are selected from the group consisting of calcium chloride, calcium sulphate and calcium acetate and the respective phosphate salts are selected from the group consisting of sodium phosphate, ammonium phosphate and sodium ammonium phosphate.

8. The product according to claim 1 further comprising from about 0.01 to about 20% by weight of triclosan.

9. The product according to claim 1 further comprising from about 0.01 to about 20% by weight of a zinc salt.

10. A method for remineralizing tooth enamel comprising:
   (A) obtaining a product comprising:
      (i) a first composition comprising from about 0.1 to about 20% by weight of a peroxide and from about 0.01 to about 30% by weight of a water soluble calcium phosphate or monolithic combination of water soluble calcium and phosphate salts, the composition having a pH less than 7; and
      (ii) a second composition comprising from about 0.01 to about 30% by weight of an alkaline material and an anticaries effective amount of a fluoride on source, the second composition having a pH greater than 7.5 and stored separately from the first composition in a manner to avoid contact between the phosphate and the alkaline material;
   (B) extruding a portion of first and second compositions onto a toothbrush; and
   (C) brushing the teeth with the combination of first and second compositions.

11. The method according to claim 10 wherein the water-soluble phosphate salt is monocalcium hydrogen phosphate.

12. The method according to claim 10 wherein the alkaline material is selected from the group consisting of sodium bicarbonate, potassium bicarbonate, sodium hydroxide, potassium hydroxide, sodium carbonate, potassium carbonate, calcium carbonate, calcium oxide and mixtures thereof.

13. The method according to claim 10 wherein the pH of the first composition ranges from 2.5 to 5.5.

14. The method according to claim 10 wherein the pH of the second composition ranges from 7.2 to 11.

15. The method according to claim 10 wherein the pH of the first composition results from inclusion of a compound selected from the group consisting of hydrogen peroxide, inorganic acids, $C_2$–$C_{20}$ carboxylic acids and mixtures thereof.

16. The method according to claim 10 wherein the monolithic combination of water soluble calcium salts are selected from the group consisting of calcium chloride, calcium citrate, calcium sulphate and calcium acetate and the respective phosphate salts are selected from the group consisting of sodium phosphate, ammonium phosphate and sodium ammonium phosphate.

17. The method according to claim 10 further comprising from about 0.01 to about 20% by weight of triclosan.

18. The method according to claim 10 further comprising from about 0.01 to about 20% by weight of a zinc salt.

* * * * *